(12) United States Patent
Rönnberg

(10) Patent No.: US 6,685,689 B1
(45) Date of Patent: Feb. 3, 2004

(54) METHOD OF PRODUCING AN OUTER SHEET THAT INCLUDES BARRIER FLAPS, AND AN OUTER SHEET PRODUCED IN ACCORDANCE THEREWITH

(75) Inventor: Peter Rönnberg, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/720,909

(22) PCT Filed: Jul. 1, 1999

(86) PCT No.: PCT/SE99/01200

§ 371 (c)(1),
(2), (4) Date: Apr. 2, 2001

(87) PCT Pub. No.: WO00/01333

PCT Pub. Date: Jan. 13, 2000

(30) Foreign Application Priority Data

Jul. 2, 1998 (SE) ............................................. 9802374

(51) Int. Cl.[7] ................................................. A61F 13/15
(52) U.S. Cl. ............................ 604/385.28; 604/385.01; 604/385.101; 604/378; 604/358
(58) Field of Search ........................ 604/385.101, 378, 604/385.28, 358, 385.01

(56) References Cited

U.S. PATENT DOCUMENTS

| | | | |
|---|---|---|---|
| 5,246,431 A | * | 9/1993 | Minetola et al. ........ 604/385.28 |
| 5,304,160 A | | 4/1994 | Igaue et al. |
| 5,413,570 A | | 5/1995 | Enloe |
| 5,662,637 A | | 9/1997 | Kitaoka et al. |
| 6,171,290 B1 | * | 1/2001 | Boisse et al. ........... 604/385.01 |
| 6,238,380 B1 | * | 5/2001 | Sasaki .................... 604/385.01 |

FOREIGN PATENT DOCUMENTS

| | | |
|---|---|---|
| EP | 0 374 640 | 6/1990 |
| EP | 0 391 476 | 10/1990 |
| JP | 2-174845 | 7/1990 |

* cited by examiner

Primary Examiner—John J. Calvert
Assistant Examiner—Angela J Grayson
(74) Attorney, Agent, or Firm—Burns, Doane, Swecker & Mathis, L.L.P.

(57) ABSTRACT

A method for producing an elongate sheet of material that includes barrier flaps which extend along the side-edges of said sheet in spaced relationship with respective side-edges, and which project up from the plane of the sheet, including placing along each edge-part of a first elongate web a narrower second elongate web, so the outer side-edges of respective second webs will lie edge-to-edge with the side-edges of the first web; placing along each edge-part of the first elongate web and on top of respective second webs a third elongate sheet narrower than the first sheet, so the outer side-edges of respective third webs will lie edge-to-edge with the side-edges of the first and second webs; joining the first, second and third webs together with a join extending along the outer side-edges of the webs; and swinging the third webs laterally outwards through 180° around the join lines.

15 Claims, 2 Drawing Sheets

METHOD OF PRODUCING AN OUTER SHEET THAT INCLUDES BARRIER FLAPS, AND AN OUTER SHEET PRODUCED IN ACCORDANCE THEREWITH

FIELD OF INVENTION

The present invention relates to a method of producing an elongate sheet of material that includes barrier flaps which extend along the side-edges of said sheet in spaced relationship with said side-edges and which project up from the plane of said sheet.

BACKGROUND OF THE INVENTION

Liquid absorbent articles, such as diapers, provided with elongate elastic elements for imparting a desired shape to the article in its use state are known to the art. In the case of diapers and incontinence protectors, which in use are donned by the wearer in a pants-like configuration, it is usual to provide so-called leg elastic which extends along the side-edges of the diaper in the crotch region thereof, so as to create, when the diaper is donned, raised elastic edges which seal tightly around the thighs of the wearer, such as to enclose discharged body liquid, or fluid, in the diaper.

It is also known to provide longitudinally extending, raised barrier flaps on the liquid receiving surface of absorbent articles. These barrier flaps function to prevent liquid flowing laterally out towards the side-edges of the article and leaking over said side-edges. Such barrier flaps are particularly effective, when the wearer lies on one side or when the wearer discharges large volumes of liquid at one and the same time. The barrier flaps also prevent lateral spreading of faeces. The barrier flaps can either be used alone or together with leg elastic.

It is known, e.g., from EP 0 391 476 to provide a diaper with raised barriers. These barriers are folded down against the absorbent body in their respective crotch centre sections and are glued in this position. This results in raised barriers whose height above the absorbent body in the crotch region is lower than the height above respective rear and front parts of the diaper, which is said to enhance wearer comfort. It is also said that the main purpose of the barriers is to provide a damming effect, whilst the actual seal against lateral leakage is comprised of the leg elastic.

U.S. Pat. No. 5,413,570 teaches another method of obtaining raised barrier flaps, which in this case are fastened on top of the outer material of the diaper. These flaps have a long-edge part which is fastened to the diaper, and a long-edge part which is free. The fastened edge-parts of the barrier flaps may be straight, whereas the free edge-parts may be curved and provided with elastic elements. Alternatively, the barrier flaps may consist of strips of uniform widths and which have been attached to the diaper with a curvature that converges towards or diverges away from the crotch section.

EP 0 374 640 teaches an alternative method of providing raised barrier flaps of varying heights. The front end-parts of the barrier flaps, which are straight originally, are folded towards the centre of the diaper and fastened thereto, whereas the rear end-parts of the flaps are folded back against the rear outer corner-parts of the diaper and there fastened. Each flap will therewith be folded towards the centre of the diaper at its front edge and out from the centre of the diaper at its rear edge.

One problem with the manufacture of absorbent articles of the aforesaid kind resides in producing raised barrier flaps on an outer sheet of such a product in a simple and cost-effective manner.

An object of the present invention is to solve this problem and, at the same time, provide a sheet of material that includes barrier flaps where the material in that part of the sheet lying between the flaps and in the parts of said sheet that lie laterally outside said flaps, and the material in the barrier flaps can be freely chosen.

SUMMARY OF THE INVENTION

This object is achieved with a method of producing an elongate sheet that includes barrier flaps which extend along the side-edges of the sheet in spaced relationship with respective side-edges, and which project up from the plane of said sheet, said method being characterised by the steps of placing along each edge-part of a first elongate sheet of material a second elongate sheet of material whose width is smaller than the width of the first sheet, such that the outer side-edges of respective second sheets will lie edge-to-edge with the side-edges of the first sheet;

placing along each edge-part of the first elongate sheet and on top of respective second sheets a third elongate sheet whose width is smaller than that of the first sheet, such that the outer side-edges of respective third sheets will lie edge-to-edge with the side-edges of the first sheet and the second sheets;

joining the first, second and third sheets together with a join that extends along the outer side-edges of said sheets; and swinging the third sheets laterally outwards through an angle of 180° around their join lines and laterally stretching the sheet composite consisting of the mutually joined first, second and third sheets, therewith raising the second sheets from the plane of the first and third sheets. Such a process can be readily incorporated in a continuous absorbent article manufacturing process without having a disturbing effect on the remainder of the process and without needing to slow down production. The equipment required to carry out the method is both simple and uncomplicated. The method thus enables barrier-carrying outer sheets to be produced in a cost-effective manner. Because the first, second and third sheets are mutually separate sheets, the materials from which these sheets are comprised may be freely chosen.

In one preferred embodiment, the second sheets are comprised of elastic material and are applied in a stretched state. In one variant, the second sheets are shorter in length than the first and third sheets, said first and third sheets comprising continuous webs of material and the second sheets being applied in pairs on the first sheet with said pairs of second sheets being spaced at a given distance apart The end-edges of the second sheets are joined to the first sheet prior to the third sheets being applied, and the various sheets are joined together by heat welding or ultrasonic welding, or are glued together.

The invention also relates to an elongate, liquid-permeable outer sheet for absorbent articles, such as diapers, incontinence protectors and sanitary napkins, said outer sheet including barrier flaps which extend along the side-edges of said sheet, at least within a longitudinal central part thereof, in spaced relationship with respective side-edges, and which project up from the plane of said sheet, said sheet being characterised in that the barrier flaps, the part of the sheet that lies between said barrier flaps, and the edge-part of the sheet lying laterally outside the barrier flaps are comprised of mutually separate and mutually joined sheets of material.

That part of the outer sheet which lies between the barrier flaps is comprised of liquid permeable material, whereas the edge-parts and the barrier flaps are comprised of liquid impermeable material. The barrier flaps are comprised of elastic material, or material that has been made elastic, and extend along the full length of the outer sheet.

In one variant, the end-edge of the barrier flaps are spaced longitudinally from respective end-edges of said sheet, and the end-edges of the barrier flaps are fastened to that part of the sheet which lies between said barrier flaps.

It will be understood that by "elastic material" is meant a material that can be stretched and that strives to return to its original form when the stretching load is removed.

BRIEF DESCRIPTION OF THE DRAWINGS

The invention will now be described with reference to the accompanying drawings, in which.

DETAILED DESCRIPTION OF EMBODIMENTS OF THE INVENTION

Figure 1:
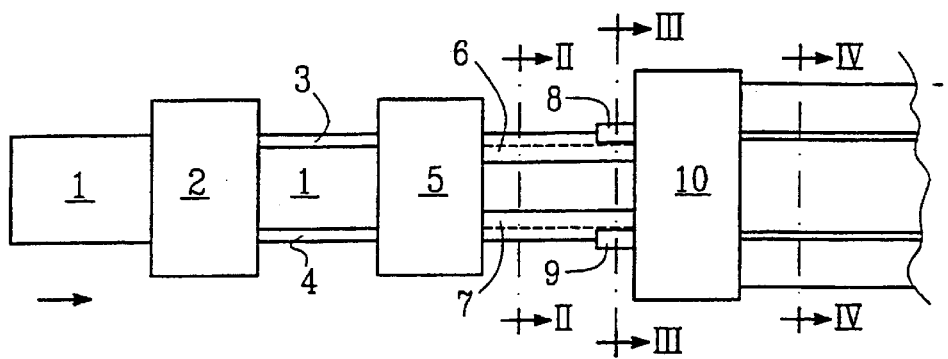
FIG. 1 is a schematic illustration of a process line for the continuous manufacture of an outer sheet of an absorbent article in accordance with one preferred embodiment of the invention.

FIG. 1 is a highly schematic illustration of a process line for the manufacture of an outer sheet in accordance with the invention. A first web 1 of material is fed from a storage reel (not shown) and is advanced by means of a conveyor (not shown) through a first station 2 in which a second web of material 3, 4 is laid on top of the first web 1 along each of its side-edge parts. The webs 3 and 4 may be reeled-up on individual storage reels, or on a common storage reel. The webs of material are then advanced through a second station 5, in which a third web of material 6, 7 is placed on top of the web 1 and the webs 3, 4, along each of the side-edge parts of the web 1. The webs 6, 7 are each taken from an individual storage reel or from a common storage reel. The outer side-edges of the second and third webs 3, 6 and 4, 7 are placed edge-to-edge with respective side-edges of the first web. The webs 1, 3, 4, 6 and 7 are then joined together along their outer side-edges with the aid of a welding unit 8, 9, and then advanced through a third station 10 in which the third webs 6, 7 are swung laterally outwards through 180° relative to the direction in which the webs are advanced, as indicated by an arrow in FIG. 1. The composite web is stretched laterally to some slight extent after the third webs have been swung outwards. The composite web comprising the mutually joined webs 1, 3, 4, 6 and 7 can then be placed on top of a further web of material included in an absorbent article production line and carrying a row of mutually separated absorbent bodies. It is, of course, also possible to wind the composite web onto a storage reel when desiring to produce the outer sheet in a place other than in an absorbent article production line.

Figure 2:
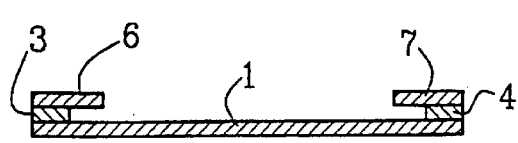
FIGS. 2–4 are respective cross-sectional views taken on the lines II—II, III—III and IV—IV in FIG. 1.

FIG. 2 is a cross-sectional view illustrating the first, second and third webs subsequent to the second webs 3, 4 and the third webs 6, 7 webs having been laid on the first web 1.

Figure 3:
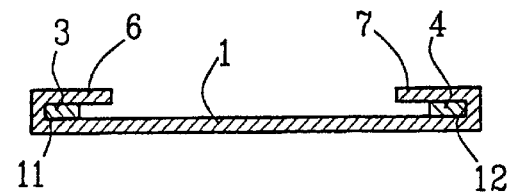

FIG. 3 is a view similar to the view of FIG. 2 and shows the webs welded together along their outer side-edges. The weld joins 11, 12 are shown schematically. Subsequent to having joined the webs together, the webs 6, 7 are swung outwards as indicated by arrows in FIG. 3.

Figure 4:
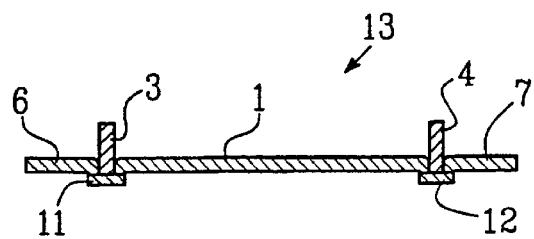

FIG. 4 shows the composite web 13 comprising said webs 1, 3, 4, 6 and 7 subsequent to the webs 6, 7 having been swung outwards from the position shown in FIG. 3 through an angle of 180°. As the webs 6, 7 are swung outwards, the web 1 also curves or bends in the proximity of the joins 11, 12, which leads to the webs 3 and 4 being swung upwards relative to the plane of the web 1. The web 13 is also stretched laterally in the final stage of swinging the webs 6, 7 outwards, or after outward swinging of said webs has been terminated, as indicated by arrows in FIG. 4. This lateral stretching of the web 13 ensures that the second webs 3, 4 will take a position in which they project up substantially at right angles to the plane of the webs 1, 6, 7.

The aforedescribed method thus enables an outer sheet 13 that includes barrier flaps 3, 4 to be readily produced. As will be evident from the aforegoing, the method is highly effective in producing a continuous web of outer sheet material and the production line described with reference to FIGS. 1–4 can be incorporated readily in a production line for the manufacture of diapers, incontinence protectors or sanitary napkins without having a disturbing effect on other parts of the production line. A further advantage afforded by this method is that it offers a free choice with respect to the materials used in the first, the second and the third webs. In the described embodiment, at least the second webs are comprised of weldable material, although this is not a necessary criterion since the joins 11, 12 can be effected with the aid of glue when welding is not a functional alternative.

The web 1 is comprised of a liquid-permeable material, preferably an hydrophilic. nonwoven. Naturally, other liquid-permeable materials used as outer sheet material in absorbent articles may be used, such as perforated plastic film, for instance.

The second webs 3, 4 will constitute barrier flaps when using an absorbent article provided with an outer sheet 13, and may beneficially be made of an elastic material so as to enable the flaps to conform readily to the shape of the wearer's body. This is not a necessary criterion, however, since it will suffice for the material from which the barrier flaps are formed to be deformable or flexible, pliable, in order for the flaps to conform to the shape of the wearer's body. When the third webs 6, 7 of such an outer sheet are comprised of a liquid-impervious material, the second webs shall also be comprised of liquid-impervious material so as to ensure that liquid is unable to reach the webs 6, 7. It may also be appropriate to produce the second webs from liquid-impervious material in other cases.

The second webs 3, 4 are preferably produced from an elastic plastic film, such as from styrene-butadiene-styrene, for instance. It is also possible to use elastic shrink film, i.e. a plastic film which shrinks when heated and therewith becomes elastic. Another option is to use a plastic film that has been made elastic by providing the film with pretensioned elastic threads or functionally similar devices. The webs 3, 4 may optionally be comprised of foam material or any suitable elastic or inelastic, compressible material enclosed in plastic film.

The webs 6, 7 are preferably produced from nonwoven material, which may be comprised of hydrophobic fibres or fibres that have been made hydrophobic. Other hydrophilic materials are also conceivable for the production of webs 6, 7, although these materials are not preferred. Any of the materials used in the liquid-impervious outer sheets of known absorbent articles are conceivable for use in this context.

The webs 1, 3, 4, 6 and 7 may even consist of several mutually laminated layers.

Figure 5:
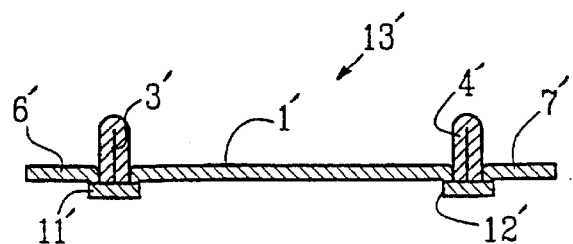
FIG. 5 is a cross-sectional view similar to the view of FIG. 4, illustrating a second embodiment of an inventive outer sheet.

FIG. 5 illustrates a second embodiment of a composite web 13'. The web 13' differs from the web 13 of the FIG. 4 embodiment solely by virtue of the fact that the second webs 3', 4' are comprised of double-folded sheets whose free edges are joined to the webs 1', 6' and 7' by joins 11', 12'. Remaining components are the same as the corresponding components of the composite web 13 and have been identified with the same reference numerals to which a prime has been added.

In the described embodiment, the second and third webs 3, 4 and 6, 7 have straight edges. However, this is not a necessary criterion and it suffices that the edges that are to be joined together and with the web 1 are straight. The opposing edges may have any desired shape, which also applies to the width of the webs. As an alternative to laying second webs continuously on the first web, pairs of pieces of second web material may be placed mutually sequentially on the first web at a determined distance apart, when the barrier flaps, formed by the second webs on an outer sheet included in an absorbent article are not required to extend along the full length of the article. When these second web pieces are comprised of plastic film incorporating prestretched elastic threads disposed along the free edge of each web piece, it may be beneficial to fasten the end-edges of each such piece to the first web in the manufacturing process and in conjunction with laying out said pieces onto the first web.

Figure 6:
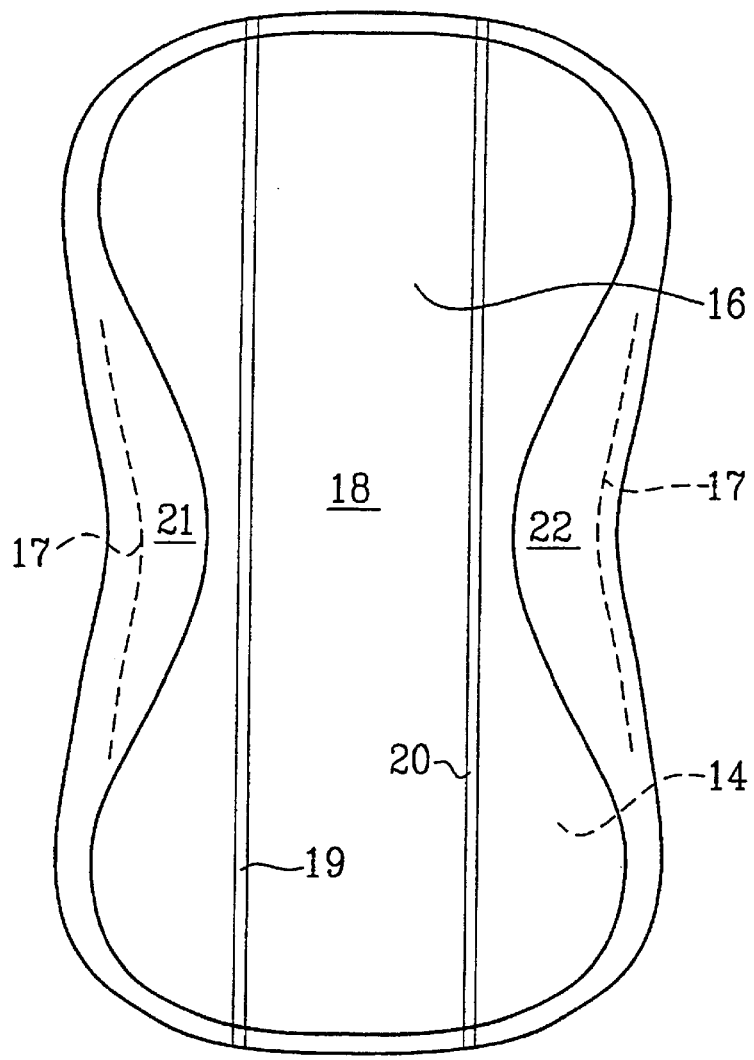
FIGS. 6 and 7 show respectively an incontinence protector or napkin that includes an outer sheet according to a third embodiment of the invention, said views being seen from above and from one side respectively.
Figure 7:
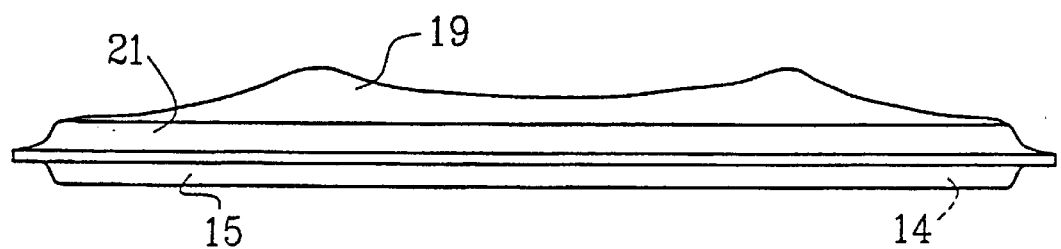

FIGS. 6 and 7 illustrate an incontinence protector provided with an outer sheet according to a third embodiment of the invention, said Figures showing the incontinence protector from above and from one side respectively. The incontinence protector is typically comprised of an absorbent body 14 which is enclosed between a liquid-permeable outer sheet 15 and an outer sheet 16 according to the invention. The outer sheets 15, 16 are joined together at parts which lie outside the absorbent body, and elastic elements 17 are provided between the edge-parts of the outer sheets in the longitudinal centre part of the incontinence protector, such as to form so-called leg elastic.

The outer sheet 16 includes a first layer of material 18 which extends across the transversal central part of the incontinence protector. Analogous with the FIGS. 4 and 5 illustrations, the outer sheet 16 includes outer sheets 13, 13', barrier flaps 19, 20 and outer material. layers 21, 22 which extend along the side-edges of the first sheet material on both sides thereof The outer sheet 16 is produced in the same way as the outer sheets 13, 13' and the layers in the outer sheet are joined together in the same way as the first, second and third webs shown in FIGS. 4 and 5. The difference between the outer sheet 16 and the earlier described outer sheets 13, 13' is that the barrier flaps 19, 20 are not straight, but have a curved form as seen from one side, as will be evident from FIG. 7. It will be understood that the described embodiments can be modified within the scope of the invention, particularly with respect to the dimensions of the second and third webs. The invention is therefore only restricted by the contents of the accompanying Claims.

What is claimed is:

1. A method of producing an elongate sheet of material having side edges, the sheet includes barrier flaps that extend along the side-edges of said sheet in spaced relationship with said side-edges and which barrier flaps project up from a plane of said sheet, the elongate sheet having at least one first elongate web of material, at least two second webs of material, and at least two third webs of material, the method comprising:

placing along each side edge of the first elongate web of material one of the second elongate webs of material whose width is smaller than a width of the first web, such that the respective outer side-edges of the second webs will lie edge-to-edge with the side-edges of the first web;

placing along each side edge of the first elongate web one of the third elongate webs whose width is smaller than the width of the first web, said third webs being placed on the respective second webs such that the outer side-edges of respective third webs will lie edge-to-edge with the side-edges of the first web and said second webs;

joining the first, second and third webs together with a join that extends along each of the outer side-edges of the webs; and swinging the third webs laterally outwards about their join lines through an angle of 180°, and stretching the elongate sheet comprising the mutually joined first, second and third webs laterally, wherewith the second webs are lifted up from the plane of the first and third webs.

2. A method according to claim 1, wherein the second webs are comprised of elastic material and attached in a stretched state.

3. A method according to claim 1, wherein the second webs are shorter in length than the first and third webs.

4. A method according to claim 3, wherein the first and third webs are comprised of continuous webs, and in that the second webs are placed in pairs on the first web, with said pairs of second webs at a predetermined distance apart.

5. A method according to claim 3, wherein the end-edges of the second webs are joined to the first web prior to placing the third webs thereon.

6. A method according to claim 1 wherein the joins between the different webs are made by heat welding or ultrasonic welding techniques.

7. A method according to claim 1, wherein the joins between the different webs of material are made by gluing.

8. An elongate, liquid-permeable outer sheet for absorbent articles, said outer sheet comprising barrier flaps that extend along side-edges of the outer sheet at least within a longitudinal central part thereof, in a spaced relationship with respective side-edges, and which project up from a plane of said outer sheet, the barrier flaps, a part of the outer sheet which lies between the barrier flaps, and edge-parts of said outer sheet lying outwardly of the barrier flaps are comprised of mutually separate webs of material, mutually joined along adjoining side edges.

9. An outer sheet according to claim 8, wherein the part of the outer sheet that lies between the barrier flaps is comprised of a liquid-permeable material.

10. An outer sheet according to claim 9, wherein the edge-parts are comprised of a liquid-impermeable material.

11. An outer sheet according to claim 10, wherein the barrier flaps are comprised of a liquid-permeable material.

12. An outer sheet according to claim 8, wherein the barrier flaps are comprised of an elastic material or of a material that has been made elastic.

13. An outer sheet according to claim 8, wherein the barrier flaps extend along the full length of said outer sheet.

14. An outer sheet according to claim 8, wherein the end-edges of the barrier flaps in the longitudinal direction are spaced from respective end-edges of said outer sheet.

15. An outer sheet according to claim 14, wherein the end-edges of the barrier flaps are fastened to that part of the outer sheet which lies between the barrier flaps.

* * * * *